United States Patent [19]

Sianesi et al.

[11] 4,174,461
[45] Nov. 13, 1979

[54] STABILIZED PERFLUOROPOLYETHER FLUIDS

[75] Inventors: Dario Sianesi; Giuseppe Nelli, both of Milan; Renzo Fontanelli, Rome; Valentino Zamboni, Busto Arsizio, all of Italy

[73] Assignee: Montecantini Edison S.p.A., Milan, Italy

[21] Appl. No.: 749,477

[22] Filed: Dec. 10, 1976

Related U.S. Application Data

[60] Continuation of Ser. No. 550,293, Feb. 18, 1975, abandoned, which is a continuation of Ser. No. 294,582, Oct. 3, 1972, abandoned, which is a division of Ser. No. 156,391, Jun. 24, 1971, abandoned.

[30] Foreign Application Priority Data

Jun. 27, 1970 [IT] Italy ............................. 26668 A/70

[51] Int. Cl.$^2$ ............................................. C07C 43/00
[52] U.S. Cl. ..................................... 568/582; 252/54; 252/77; 260/557 B; 260/558 A; 260/558 P; 260/559 R
[58] Field of Search ................. 260/611.5; 568/580, 568/581, 582

[56] References Cited

U.S. PATENT DOCUMENTS

| | | | |
|---|---|---|---|
| 3,250,806 | 10/1970 | Sianesi et al. | 260/535 H |
| 3,250,807 | 10/1966 | Fritz et al. | 260/535 H |
| 3,250,808 | 10/1966 | Moore et al. | 260/535 H |
| 3,274,239 | 10/1966 | Selman | 260/535 H |
| 3,393,151 | 7/1968 | Dolle et al. | 260/611.5 X |
| 3,493,530 | 2/1970 | Sianesi et al. | 260/561 |

*Primary Examiner*—Bernard Helfin
*Attorney, Agent, or Firm*—Hubbell, Cohen, Stiefel & Gross

[57] ABSTRACT

Perfluoropolyether compounds and mixtures thereof having the formula:

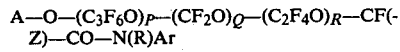

A—O—$(C_3F_6O)_P$—$(CF_2O)_Q$—$(C_2F_4O)_R$—CF(-Z)—CO—N(R)Ar wherein the perfluoroalkyleneoxy groups are randomly distributed and A is a perfluoroalkyl group or a —CF(-Z)—CO—N(R)Ar group; P, Q and R are zero but not simultaneously or numbers from 1 to 100, the sum of P, Q and R being 3 to 200; Z is a fluorine atom or a $CF_3$ group; Ar is an aryl group; and R is hydrogen, alkyl, alkyl-aryl or an aryl group.

These compounds are excellent stabilizers for perfluoropolyether fluids of the formula:

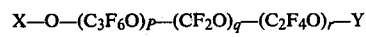

X—O—$(C_3F_6O)_p$—$(CF_2O)_q$—$(C_2F_4O)_r$—Y wherein p, q and r are each zero or numbers from 1 to 100, the sum of p, q and r being 6 to 200, and X and Y are the same or different and are perfluoroalkyl groups having 1 to 3 carbon atoms.

2 Claims, 2 Drawing Figures

STABILIZED PERFLUOROPOLYETHER FLUIDS

This is a continuation of application Ser. No. 550,293, filed Feb. 18, 1975, and now abandoned which is a continuation of Ser. No. 294,582, filed Oct. 3, 1972 and now abandoned, and which is a division of Ser. No. 156,391, filed June 24, 1971, and now abandoned.

BACKGROUND OF THE INVENTION

1. Field of the Invention

The present invention relates to mono- and diarylamide perfluoropolyether compounds and to compositions thereof with perfluoropolyether fluids, said compositions having improved resistance to degradation caused at high temperatures by the action of metals and oxygen and by metal oxides. The compositions are prepared by adding arylamide derivatives of mono- and dicarboxylic perfluoropolyether acids to the perfluoropolyether fluid.

2. Description of the Prior Art

The continuing development of the technology of processing machinery and of transportation, especially in the aeronautical field, requires metal materials capable of withstanding stresses at higher and higher temperatures. In particular applications, these metal materials are in contact with non-metallic materials, such as antifriction agents, lubricants and heat exchange means all of which must be capable of resisting vigorous operating conditions. In particular, lubricating fluids having greater thermal stability and resistance to oxidation than those of the conventional products now available are required.

The requirement for lubricating and heat exchange fluids capable of withstanding, for long periods and without excessive alteration, high temperatures and high shearing stresses, has led to the synthesis and formulation of new fluids.

For this purpose, perfluorinated compounds are particularly suitable because of their high resistance to high temperatures. The perfluorinated polyethers constitute one of the most important classes of high viscosity perfluorinated fluids, since they combine the good characteristics of thermal stability and oxidation resistance with viscosity indices and low temperature characteristics comparable to or better than those of mineral oils.

The polyperfluoroether fluids, mixtures thereof and processes for their preparation have heretofore been described, for instance, in Italian Pat. No. 793,154; Canadian Pat. No. 810,750; and U.S. Pat. No. 3,214,478.

They consist of linear molecules containing, in their chain, repeating perfluoroalkylene units, which may be the same or different from one another and which contain from 1 to 3 carbon atoms, mutually linked through an ether linkage; generally, the terminal groups of the chains are perfluoroalkyl radicals.

The polyperfluoroether fluids have the following general formula:

$$X-O-(C_3F_6O)_p-(CF_2O)_q-(C_2F_4O)_r-Y \qquad (I)$$

wherein $-C_3F_6-$ and $C_2F_4-$ are perfluoroalkylene groups derived, respectively, from the opening of the double bonds of hexafluoropropylene and tetrafluoroethylene, respectively, and when different perfluoroalkylenoxy units are simultaneously present, they are randomly distributed along the chain; p, q and r are average composition indices, the sum of which is between 6 and 200; each of p, q and r can be zero but not simultaneously or a number ranging from 1 to 100; X and Y are identical or different terminal groups and generally are perfluoroalkyl radicals containing from 1 to 3 carbon atoms. These polyperfluoroethers containing from 6 to 200 perfluoroalkylenoxy repeating units are endowed with fluidity characteristics at room temperature which are typical of either fluid or lubricating greases or hydrodynamic or heat exchange fluids.

Some of these fluids are stable for long periods of time at temperatures of 420°–450° C. However, it has been found that at temperatures around 250° C., i.e. at temperatures considerably lower than that of the thermal stability of the bonds present in the chain, these fluids, when put into contact with certain metal materials in common use and in the presence of air, undergo remarkable degradation such as a decrease in viscosity and a loss of weight of the material in the form of poisonous and corrosive gases.

Moreover, in the thus degraded fluid, there appear acid type functions which may have corrosive effects on the metals. Particularly severe degradative effects have been observed in the presence of titanium, aluminum, alloys thereof and certain steels.

Similar degradation phenomena occur to a greater extent when the perfluoropolyether fluids are heated at temperatures higher than 250° C. in the presence of metal oxides. In addition, it has been noted that, contrary to what occurs in the presence of metals, degradation also occurs in the presence of oxides in a non-oxidizing atmosphere such as, for instance, under vacuum or in a $N_2$ or $CO_2$ atmosphere.

In view of this degradation, it is necessary to incorporate into the fluid small amounts of materials having functional groups which exert a stabilizing action with respect to the above mentioned degrading agents. For this purpose, it is known that additives, i.e., chemical compounds which exert specific and characteristic actions directed toward improving certain properties of a fluid, are largely used in the field of hydrocarbon based normal fluids and lubricating oils.

On the other hand, in the present case, for various reasons, it is not always convenient to employ as stabilizing additives those compounds normally used for the stabilization of hydrocarbon fluids. In fact, in order to be useful as a stabilizer for perfluoropolyether fluids, the stabilizing compound must be compatible with and sufficiently soluble or miscible in said fluids at room temperature, and it is known that the perfluorinated liquids have very poor compatibility and miscibility with respect to non-completely fluorinated compounds. Furthermore, the stabilizing compound must itself have a very high thermal resistance and a minimun volatility because of the high temperatures at which it is used; and it must not significantly alter, by its presence, the basic properties of the fluid, such as for instance, the viscosity, the lubricating power and the resistance to chemical agents.

Lastly, during its action, the stabilizer must not give rise to any significant carbon formation or formation of fluid-insoluble by-products.

SUMMARY OF THE INVENTION

The invention, in one aspect thereof, is a class of perfluoropolyether compounds having the formula:

$$A-O-(C_3F_6O)_p-(CF_2O)_q-C_2F_4O)_R-CF(Z)-CO-N(R)Ar \qquad (II)$$

wherein A is a perfluoroalkyl group having 1 to 3 carbon atoms or a —CF(Z)—CO—N(R)Ar group, and the three different perfluoroalkylenoxy groups are randomly distributed along the chain; P, Q and R are each zero but not simultaneously or a number ranging from 1 to 100, the sum of P, Q and R being 3 to 200; Z is a fluorine atom or a $CF_3$ group; Ar is an unsubstituted aryl group or an aryl group substituted with an alkyl group, an aryl group or a halogen in one, two or three positions of the aromatic ring; and R is hydrogen, an alkyl group, an alkylaryl group or an aryl group bound to Ar either directly or through a hetero atom.

The perfluoropolyether compounds of the invention are therefore linear polymers which can otherwise be characterized as containing from 3 to 200 repeating units of any combination of one or more of the perfluoroalkyleneoxy groups of the formula:

$(C_3F_6O)$, $(CF_2O)$ and $(C_2F_4O)$.

The terminal groups of the polymer are A and —CF(Z)—CO—N(R)Ar, wherein A, Z, R and Ar are as defined above.

In another aspect, the invention is a stabilized composition comprising at least one perfluoropolyether compound of the formula (I) in combination with a stabilizing amount of at least one compound of the formula (II).

DETAILED DESCRIPTION

According to the present invention, it has now been found that all the requirements for a compound suitable for stabilizing polyperfluoroethers described above in connection with the prior art are met by a new class of compounds, which, broadly speaking, are arylamides of mono- or dicarboxylic acids.

The compounds of the present invention have the following general formula:

A—O—$(C_3F_6O)_P$—$(CF_2O)_Q$—$(C_2F_4O)_R$—(CF(Z)—CO—N(R) Ar    (II)

wherein A is a perfluoroalkyl group having 1 to 3 carbon atoms, or a —CF(Z)—CO—N(R)Ar group ($C_3F_6$ and $C_2F_4$ being perfluoroalkylene groups derived respectively from the opening of the double bond of hexafluoropropylene or tetrafluoroethylene) and the three different perfluoroalkylenoxy units are randomly distributed along the chain; P,Q and R are composition indices, the sum of which is a value of 3 to 200 and each of P,Q and R can be zero but not simultaneously or a number ranging from 1 to 100; Z is a fluorine atom or a $CF_3$ group; Ar is an unsubstituted aryl group or an aryl group substituted with an alkyl, aryl or halogen in one, two or three positions of the aromatic ring; and R is a hydrogen atom, an alkyl group, an alkylaryl group or an aryl group bound to Ar either directly or through a hetero atom.

The above described compounds are miscible in the perfluoropolyether fluids at room temperature and are also stable in the presence of oxygen and metals up to temperatures in the range of 400° C. When introduced in suitable concentrations in the perfluoropolyether fluids, they produce compositions characterized by excellent resistance to thermooxidative degradation catalyzed by metals or their oxides.

The stabilized compositions according to the present invention therefore comprise: (A) at least one perfluoropolyether fluid of the formula (I), and (B) a stabilizing amount of at least one compound of the formula (II). Component (B) is generally used in an amount greater than 0.01 part by weight per 100 parts of the component (A).

The compounds of formula (II) may be prepared by various methods. We have found it preferable to use a process comprising reacting an aromatic amine of the formula Ar(R)NH, wherein Ar and R are as defined above, with a derivative of a mono- or dicarboxylic acid having the following formula:

B—O—$(C_3F_6O)_P$—$(CF_2O)_Q$—$(C_2F_4O)_R$—CF(Z)—CO—M    (III)

wherein P, Q, R and Z are as defined above and B is a perfluoroalkyl radical having 1 to 3 carbon atoms, or a —CF(Z)COM group wherein M is a halogen atom or an alkoxy group of the formula OR', wherein R' is a lower alkyl radical, such as, for instance, methyl.

These mono- and dicarboxyl perfluoropolyether derivatives may be obtained either directly or by a series of reactions which are all known. These processes are described in several patents, such as, for example, Italian Pat. Nos. 641,274, 773,214, 773,920, 774,001, 789,220 and 817,809, and U.S. Pat. Nos. 3,125,599, 3,250,807, and 3,250,808. The derivatives of the formula (III) may be used alone as pure compounds, thus forming, by the reaction with the aromatic amine, arylamides having a perfectly defined structure. They may also be used in the form of mixtures of homologues and isomers, and in this case they form arylamide mixtures of perfluoropolyether acids having average values of molecular weight and composition.

The present invention also relates to the use of the above mentioned derivatives of mono- and dicarboxyl perfluoropolyether acids in admixture with one another, also in the presence of perfluoropolyethers which do not contain acid type terminal groups, which consequently during the reaction with the amine behave as inert diluents and which, subsequently, when in admixture with the arylamides of formula (II), are part of the formulation of the stabilized fluids.

The reaction between the aromatic amine and the perfluoropolyether carboxy derivative (III) may be carried out in the absence of diluents or in the presence of organic solvents of various types, that are inert under the reaction conditions and are, for example, selected among ethers, hydrocarbons and halogen substituted hydrocarbons. The carboxyl derivative (III) and the amine may be reacted with each other in stoichiometric amounts but in general it is preferable to use an excess of up to 100% amine which, at the end of the reaction, may be easily removed. The reaction temperature is preferably in the range of from 0° to 200° C., when the perfluoropolyether derivative is in the form of an acyl halide, i.e., when M is a halogen, while it is preferably in the range of from 100° to 300° C., when an ester is used, i.e., when M is OR'. The duration of the reaction is affected by the other reaction conditions. Generally several hours of reaction are sufficient to effect a practically complete conversion to the amides of formula (II).

The stabilizing action exerted by the above mentioned compounds with respect to the thermooxidative degradation of the perfluoropolyether fluids appears to be related to the presence of the arylamide group contained therein. In fact, it has been found that perfluoropolyether amides having a $CONH_2$ group, as well as amides that are N-substituted with only alkyl or cycloalkyl radicals, exert either no stabilizing action or only very poor stabilizing action. The compounds containing aromatic groups which are not directly bound to the amide nitrogen atom, such as, for instance, the dibenzylamides and the N'-aryl substituted hydrazides of the perfluoropolyether acid are also not very effective.

Generally, the stabilizing effectiveness of the arylamides of perfluoropolyether acids (II) appears to increase as the concentration of the aryl substituted amide nitrogen atoms increases, and it appears to also be favored by an increase in the number and dimensions of the aryl groups. Thus, with the weight concentration being equal, it is preferable to use as stabilizing additives, the arylamide derivatives containing in their molecule a perfluoropolyether chain of reduced length, containing for instance, less than 10 perfluoroalkyleneoxy units for every arylamide group, the latter group containing from one to four benzene nuclei, optionally at least partially condensed with one another, and preferably two benzene nuclei. In fact, compounds of this structure effectively stabilize the perfluoropolyether fluids even if added thereto in concentrations ranging from 0.01–0.1% by weight. In any event, as the ratio between the weight of the arylamide groups and the weight of the perfluoropolyether chain decreases, the miscibility of this class of compounds in the fluorinated fluid decreases. The preferred compounds according to the present invention are therefore the perfluoropolyether arylamides containing in their molecules a higher number of perfluoroalkylene units, for instance, between 10 and 100 units for each arylamide group. These compounds are generally liquid and miscible at room temperature in all ratios with the fluorinated fluids and, moreover, they show a very low volatility even at high temperatures. The improvement in the properties of resistance of the perfluoropolyether fluids to thermooxidative degradation catalyzed by metals and their oxides achieved with these additives increases with an increase in the amount of added arylamide compound, and more specifically, with an increase in the amount of arylamide groups introduced with the additive.

The additives of the preferred structure are added to the perfluorinated fluid in such a way that the stabilized compositions contain from 0.1 to 50 parts by weight of additive and preferably from 1 to 20 parts by weight per 100 parts of perfluoroether fluid. Within these ranges, the composition of any particular stabilized fluid is selected on the basis of the conditions under which it will be used, and the particular structure of the additive used. It must also be noted that the compounds according to the present invention containing a relatively high number, for instance, from 20 to 200 units of perfluoroalkylene for each terminal arylamide group, constitute by themselves a class of perfluoropolyether fluids having excellent characteristics of thermal and thermooxidative stability, good behavior with respect to viscosity variation with temperature and good lubricating power.

Therefore, they can also be used by themselves as inert fluids having good characteristics, particularly when the maximum resistance to fluid degradation caused by metals and their oxides is desired.

The effectiveness of the stabilizers of the present invention has been evaluated by the known microoxidation-corrosion test (m O-C) which is carried out in apparatus similar to that described in WAAD "Microoxidation-Corrosion Test of High Temperature Fluids", Fluids and Greases Section, Aeronautical Systems Division, Wright-Patterson Air Force Base (U.S.A.).

This test permits the evaluation of both the alterations of the characteristics of the fluid under examination and the corrosion suffered by several metals simultaneously present in the fluid.

Figure 1:
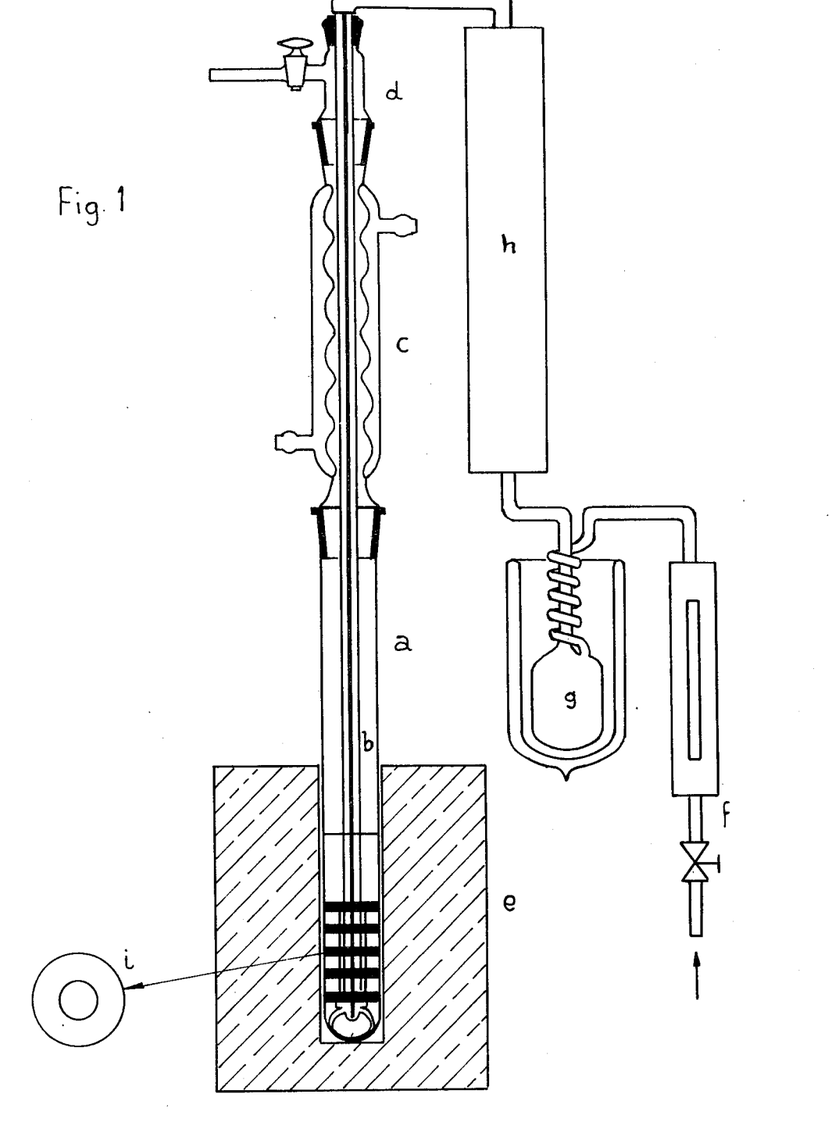
FIG. 1 is a diagrammatic illustration of the apparatus used in testing the stabilizer compounds of the invention.

The apparatus used (completely made of Pyrex glass) is shown in detail in FIG. 1: it consists of a test tube (a), a bored rod (b) on which the metal specimens (i) are placed having the shape of discs of 19 mm diameter, and a thickness of 1 mm, and a central hole of 6.3 mm, a condenser (c) on which a seal connection (d) is mounted, a metal heating block (e) provided with a thermostat which allows the temperature to be kept constant within $\pm 1°$ C., a source of high purity compressed air, a gas flow adjusting device (f), an air drying system comprising a trap (g) cooled with methanol and dry ice and a purifier (h) filled with silica gel and soda lime.

The composition of the metal specimens is given in the following Table A.

TABLE A

| CHEMICAL COMPOSITION OF THE METAL MATERIALS USED | |
|---|---|
| Material | Elements (% by weight) |
| 1) Titanium alloy | Titanium + 6.04 Al + 4.31 V + 0.0066 $O_2$ + 0.014 C + 0.006 N + 0.0005 H |
| 2) Aluminum alloy | Aluminum + 4.15 Cu + 1.47 Mg + 0.55 Mn + 0.018 Ti + 0.32 Fe + 0.15 Si + 0.037 Zn |
| 3) Tool steel | Iron + 8.01 Mo + 3.86 Cr + 2.94 W + 0.93 V + 0.63 C |
| 4) Silver | Purity 99.9% |
| 5) Stainless steel | Iron + 17.85 Cr + 10.0 Ni + 0.06 C |

The stability tests were conducted with the apparatus described according to the standard procedures given below under the following conditions:

Temperature: 316° C.
Air flow: 1liter/hour

In the test tube together with the rod and the metals, 20 ml of a stabilized formulation of perfluoropolyether are weighed and then the flow of air is adjusted. The metallic discs used in the tests were previously cleaned and polished metallurgically and washed in suitable solvents; the discs weighed on an analytical balance are inserted on the central rod suitably spaced in the order given in Table A from the top to the bottom of the test tube and they are completely covered by the fluid with an excess of about one third by the volume.

The test tube is introduced for one half of its length into the pre-heated metal block. At the end of the thermal treatment, the test tube, with the metal-bearing rod, is weighed again at room temperature; the discs are extracted, washed with $CF_2Cl-CFCl_2$ and dry-cleaned on a rotating felt cloth to remove the detachable slags, and individually weighed.

For each test the following evaluations are carried out:

1. percentage of loss in fluid weight (expressed in % of the starting weight),
2. percentage variation of the fluid viscosity measured at 20° C., and
3. weight variation of the metallic discs per surface unit (mg/cm$^2$) after the removal of the friable slags.

In order to evaluate the stabilizing properties of the additives, a more rapid test was also carried out, which proved to be equally significant.

The test consists of measuring the increase in stability due to the addition of an additive to the perfluoroether fluid heated to 365° C. in the presence of Al$_2$O$_3$ powder. The choice of this oxide was made because of its capacity for decomposing the perfluoroether fluids at a surprising rate (weight loss greater than 5% per minute) at temperatures dependent on the perfluoropolyether structure, but generally lower than 300° C.

It has also been found that a stabilizer suitable for inhibiting the fluid degradation induced by Al$_2$O$_3$, is also capable of inhibiting the degradation caused by metals in the presence of oxygen.

Figure 2:
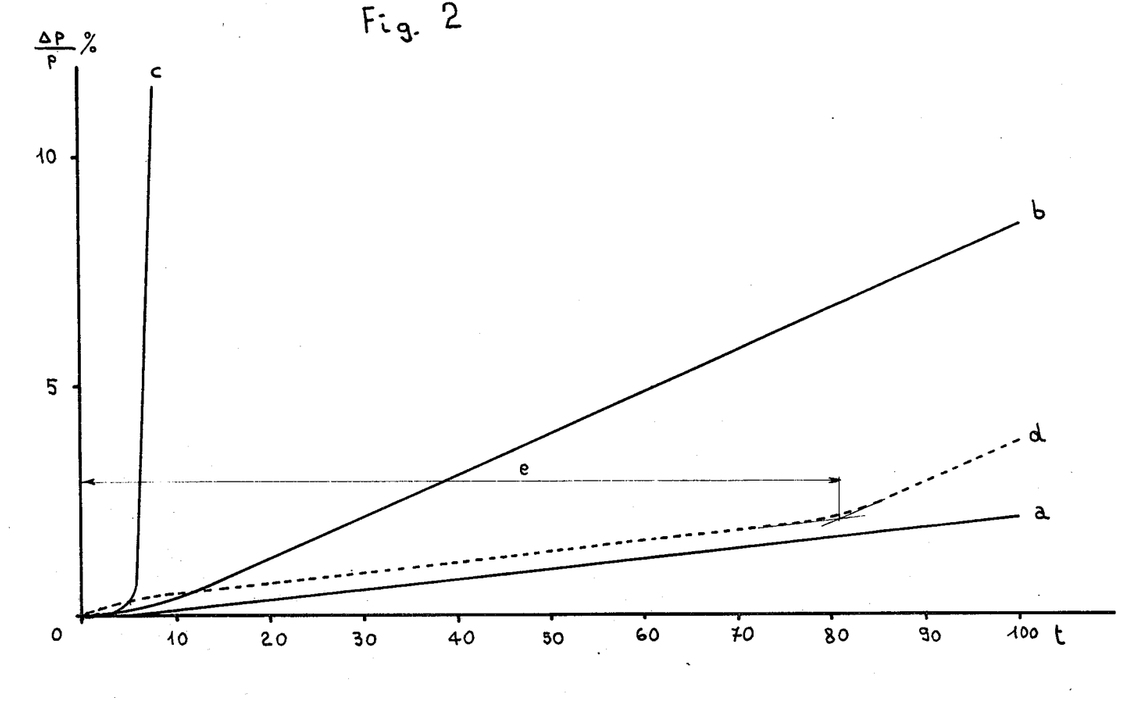
FIG. 2 is a graphical representation of the results of tests on the stability of the stabilized compositions of the invention.

The typical trends of the percent weight loss ($\Delta$ P%/P) of a perfluoroether versus time (t) in minutes relative to an isothermal analysis, are shown in FIG. 2 where curve (a) relates to the fluid decomposition in an inert atmosphere, curve (b) to the decomposition in an oxidizing atmosphere (air), curve (c) to the decomposition in air in the presence of traces of Al$_2$O$_3$ powder, and curve (d) represents the behavior in air of the fluid containing a stabilizer and the same amount of Al$_2$O$_3$. As may be seen, the stabilizing effect is that of imposing an inhibition period (e) during which the decomposition rate in air of the fluid containing Al$_2$O$_3$ is reduced to the rate of the same fluid treated in an inert atmosphere and in the absence of Al$_2$O$_3$.

From the experimental data of the inhibition period at 365° C., the time required by the sample to attain the test temperature, was found to be generally 10 minutes.

Furthermore, it was found that, even beyond the inhibition period, the stabilizer is very often able to maintain for a prolonged period of time the decomposition rate at levels lower than those which would be reached, in the absence of the stabilizer itself, even in the absence of Al$_2$O$_3$. The stability tests according to this method, were carried out using the technique described below.

1 g of a stabilized composition of polyperfluoroether fluid and a weighed quantity of Al$_2$O$_3$ were placed in a Pyrex glass flask having a volume of 5 ml, a neck of 50 mm in length and a diameter of 3 mm.

The flask was then introduced into a thermobalance preheated at 365° C. and the weight variations of the sample were continuously recorded. Using the same procedures, tests were conducted on fluids without additives in inert or oxidizing atmospheres.

The following examples will further illustrate the present invention, without, however, limiting the scope thereof. Unless otherwise indicated, all parts are by weight.

EXAMPLE 1

The starting material was a mixture of polyperfluoroether derivatives having an average chain structure —(C$_3$F$_6$O)$_P$—(CF$_2$O)$_Q$— in which P+Q=about 30 and P/Q=about 40, with terminal groups consisting of —CF$_3$ radicals and of the same number of functional groups having a structure consisting mainly of —CF$_2$—COF and In addition, terminal groups having the following structure —CF$_2$—CO—CF$_3$ were also present, but to a much lower extent. The preparation of the arylamide derivative in this example and in the following ones was carried out using the following procedure.

1200 grams of the above mentioned material were mixed at room temperature with one mole of an amine derivative hereunder specified; the mixture was vigorously stirred in a reactor in a dry atmosphere and it was heated at a temperature between 100° and 200° C., for a time ranging from 4 to 8 hours, sufficient to complete the reaction of the —COF terminal groups. Then it was cooled to room temperature and filtered on a porous diaphragm, thus removing the amine hydrofluoride formed in the reaction and any excess amine that is solid at room temperature. The filtrate was heated to 320° C./0.3 Tor, thus distilling away all traces of the starting amine. The residue was filtered on a porous diaphragm to obtain, in each instance, generally from 1100 to 1200 grams of a viscous limpid liquid with a nitrogen content between 0.19 and 0.21%. I.R. and N.M.R. examination indicated that the liquid polymer contained amide and perfluoroalkyl terminal groups. The liquid was miscible in all proportions with polyperfluoroether fluids.

Using this method, with carbazole as the amino derivative, a compound was prepared for use in the test. The compound was mixed in different amounts with different perfluoroether fluids designated Fluids I, II, III, IV and V, the compositions of which are given below. The test was carried out in the presence of Al$_2$O$_3$.

The results of the tests conducted on the resulting mixtures are given in Table 1.

Fluid I: average composition X—O—(C$_3$F$_6$O)$_{50}$(CF$_2$O)$_2$—Y wherein X and Y are —CF$_3$(85%), —C$_2$F$_5$(5%), —C$_3$F$_7$(10%).

Fluid II: average composition X—O—(C$_2$F$_4$O)$_{30}$—(CF$_2$O)$_{80}$—Y wherein X and Y are —CF$_3$(75%) and —C$_2$F$_5$(25%).

Fluid III: average composition X—O—(C$_3$F$_6$O)$_{35}$—Y wherein X and Y are —C$_3$F$_7$(50%), —C$_2$F$_5$(50%).

Fluid IV: average composition X—O—(C$_2$F$_4$O)$_{20}$—O—(CF$_2$O)$_{10}$—Y wherein Y and X are —CF$_3$(60%) and —C$_2$F$_5$(40%).

Fluid V: average composition X—O—(C$_3$F$_6$O)$_{30}$—O—(C$_2$F$_4$O)$_{20}$—Y wherein X and Y are —CF$_3$(60%), —C$_2$F$_5$(30%) and —C$_3$F$_7$(10%).

All of these fluids when subjected separately to heating at 365° C. in the presence of Al$_2$O$_3$ suffered very rapid degradation with a decomposition rate greater than 5%/min.

TABLE 1

INHIBITION PERIOD AT 365° C. IN AIR WITH 5% BY WEIGHT OF $Al_2O_3$. STABILIZER DERIVED FROM CARBOZOLE

| % by weight of stabilizer in the composition | Inhibition period (I.P.), minutes | | | | | Rate of loss in weight (% per minute) during the I.P. | | | | |
|---|---|---|---|---|---|---|---|---|---|---|
| | Fluid I | Fluid II | Fluid III | Fluid IV | Fluid V | Fluid I | Fluid II | Fluid III | Fluid IV | Fluid V |
| 0 | 0 | 0 | 0 | 0 | 0 | >5 | >5 | >5 | >5 | >5 |
| 2 | 75 | 80 | 70 | 80 | 65 | $2.1 \times 10^{-2}$ | $2.0 \times 10^{-2}$ | $2.2 \times 10^{-2}$ | $1.8 \times 10^{-2}$ | $2.3 \times 10^{-2}$ |
| 5 | 170 | 175 | 165 | 175 | 165 | $1.7 \times 10^{-2}$ | $1.6 \times 10^{-2}$ | $1.7 \times 10^{-2}$ | $1.6 \times 10^{-2}$ | $1 \times 7 \times 10^{-2}$ |
| 10 | 330 | 345 | 325 | 350 | 320 | $0.9 \times 10^{-2}$ | $0.8 \times 10^{-2}$ | $1 \times 0 \times 10^{-2}$ | $0.7 \times 10^{-2}$ | $0.8 \times 10^{-2}$ |

The stabilizer alone at 100%, under the same conditions, had an inhibition period longer than 600 minutes and a rate of loss in weight of $0.2 \times 10^{-2}$% per minute.

EXAMPLES 2-15

Starting from the same polyperfluoroether derivative described in Example 1, and from different aromatic amino compounds, and following the same procedure as in Example 1, a series of arylamides were prepared which were mixed in an amount of 5% by weight with the polyperfluoroether fluid defined above as Fluid I, and subjected to the test in the presence of $Al_2O_3$ at 365° C.

The results of these tests are reported in Table 2 where there are listed the arylamines from which the arylamides of the invention are derived.

TABLE 2

INHIBITION PERIOD AT 365° C. IN AIR IN THE PRESENCE OF 5% BY WEIGHT OF $Al_2O_3$

| Example No. | Amine used in the synthesis of the arylamide compound | Inhibition Period (min.) | Rate of loss in weight during the I.P. (% min.$^{-1}$) |
|---|---|---|---|
| 2 | aniline | 80 | $2.0 \times 10^{-2}$ |
| 3 | diphenylamine | 160 | $1.5 \times 10^{-2}$ |
| 4 | beta-haphthylamine | 120 | $1.6 \times 10^{-2}$ |
| 5 | ortho-dichloroaniline | 50 | $3.9 \times 10^{-2}$ |
| 6 | para-nitroaniline | 50 | $6.9 \times 10^{-2}$ |
| 7 | ortho-phenylaniline | 210 | $1.2 \times 10^{-2}$ |
| 8 | triphenyl-para-toluidine | 190 | $1.5 \times 10^{-2}$ |
| 9 | N-phenyl-2-naphthyl-amine | 220 | $1.2 \times 10^{-2}$ |
| 10 | phenothiazine | 240 | $1.0 \times 10^{-2}$ |
| 11 | 1-aminoanthraquinone | 135 | $1.8 \times 10^{-2}$ |
| 12 | 2-amino-fluorene | 110 | $1.9 \times 10^{-2}$ |
| 13 | N-methylaniline | 130 | $1.8 \times 10^{-2}$ |
| 14 | 1-amino-anthracene | 230 | $1.2 \times 10^{-2}$ |
| 15 | N-butylaniline | 110 | $1.9 \times 10^{-2}$ |

The stabilizer prepared according to Example 3 from diphenylamine, mixed in the ratio of 5% by weight in Fluid I was subjected to the microoxidation-corrosion test described hereinbefore, yielding the results given in Table 3.

TABLE 3

Microoxidation-Corrosion Test at 316° C. for 24 Hours in a Flow of 1 1/H of Dry Air in the Presence of Standard Series of Metals and Metal Alloys

| Loss % in weight | Variation % of viscosity | Weight variation of the metals (mg/cm$^2$) | | | | |
|---|---|---|---|---|---|---|
| | | Ti alloy | Al alloy | Tool steel | Silver | Stainless steel |
| 3.6 | +4.2 | +0.146 | +0.052 | +0.000 | +0.000 | +0.129 |

Comparative Example 1

The same test of the above described microoxidation corrosion carried out in Fluid I without additives gave the following results:

| Loss % in weight | Variation % of viscosity | Weight variation of the metals (mg/cm$^2$) | | | | |
|---|---|---|---|---|---|---|
| | | Ti alloy | Al alloy | Tool steel | Silver | Stainless steel |
| 37.5 | −93 | −0.924 | +0.081 | −0.276 | −0.642 | +0.454 |

Comparative Examples 2-13

Using the same procedures as described in the preceding examples, different amides were prepared starting from the same mixture of carboxylic derivatives having a perfluoropolyether structure (formula III), which amides, however, did not contain aromatic nuclei bound directly with the nitrogen of the amide. Each of these derivatives was added in an amount corresponding to 5% by weight to a perfluoroether fluid of the type indicated above as I, and the effectiveness in inhibiting the fluid degradation provoked by $Al_2O_3$ at high temperature was determined using the above described method. The results are given in Table 4, which shows that none of these derivatives exerts a stabilizing action comparable to that of the arylamide derivatives according to the invention and described in the preceding examples.

TABLE 4

INHIBITION PERIOD AT 365° C. IN AIR IN THE PRESENCE OF 5% BY WEIGHT OF $Al_2O_3$

| Comparative Example No. | Amine used in the synthesis of the amide compound | Inhibition Period (minutes) | Rate of loss in weight during the I.P. (% per minute) |
|---|---|---|---|
| 2 | hydrazine | 0 | >5 |
| 3 | phenylhydrazine | 30 | $99.1 \times 10^{-2}$ |
| 4 | phenylurea | 15 | $09.5 \times 10^{-2}$ |
| 5 | ammonia | 0 | >5 |
| 6 | imidazole | 30 | $8.8 \times 10^{-2}$ |
| 7 | 2-aminopyridine | 10 | $10.0 \times 10^{-2}$ |
| 8 | dibenzylamine | 35 | $9.0 \times 10^{-2}$ |
| 9 | phenylsemicarbazide | 10 | $10.2 \times 10^{-2}$ |
| 10 | triphenylaminomethane | 40 | $8.2 \times 10^{-2}$ |
| 11 | cyclohexylamine | 15 | $10.8 \times 10^{-2}$ |
| 12 | piperidine | 25 | $9.6 \times 10^{-2}$ |
| 13 | 2-aminothiazole | 20 | $9.8 \times 10^{-2}$ |

EXAMPLE 16

The starting material was a polyperfluoroether functional derivative having the general formula $$-CH_3OOC-CF_2-O-(CF_2O)_Q-(C_2F_4O)_R-CF_2-COOCH_3$$

wherein Q+R=38, R/Q=0.56, molecular weight: 3090.

The material was a mixture of diesters in which the molecular weights were in the range of from about 800 to about 6,000.

25 g of this mixture of diesters and 0.04 mole of a primary aromatic amine were stirred and heated in a reactor flushed by a weak flow of nitrogen sufficient to remove $CH_3OH$ which formed during the reaction, at a temperature between the melting point and the boiling point of the amine, i.e., around 180° C., for a period of about 10 hours, sufficient to complete the substitution of the terminal —$OCH_3$ groups by amide groups. The progress of the substitution can be clearly followed by IR analysis of samples drawn at time intervals. The final mixture was heated to 320° C./0.2 Tor to distill away the excess amine. The residue of about 25 g consisted of an almost colorless limpid liquid, with a percentage nitrogen content ranging from 0.80 to 0.85.

The sole presence of amide terminal groups was confirmed by NMR analysis.

The compound obtained in this way by using as the amino derivative o-phenylaniline and tested in the presence of $Al_2O_3$, as such or mixed in various proportions with the above defined Fluid I, yielded the results shown in Table 5.

TABLE 5

INHIBITION PERIOD AT 365° C. IN AIR IN THE PRESENCE OF 5% BY WEIGHT OF $Al_2O_3$

| Compound prepared from o-phenyl-aniline % | Fluid I | Inhibition Period (minutes) | Rate of loss in weight during the I.P. (% per minute) |
|---|---|---|---|
| 100 | — | >600 | $0.2 \times 10^{-2}$ |
| 2 | 98 | 185 | $1.6 \times 10^{-2}$ |
| 5 | 95 | 410 | $0.5 \times 10^{-2}$ |

The same compound obtained from o-phenylaniline mixed in the ratio of 5% by weight with Fluid I was subjected to the microoxidation-corrosion test described above, yielding the results shown in Table 6.

TABLE 6

MICROOXIDATION-CORROSION TEST AT 316° C. FOR 24 HOURS IN A DRY AIR FLOW IN THE PRESENCE OF STANDARD SERIES OF METALS AND METAL ALLOYS

| Loss % in weight | Variation % of viscosity | Variation of weight of the metals (mg/cm²) | | | | |
|---|---|---|---|---|---|---|
| | | Ti alloy | Al alloy | Tool steel | Silver | Stainless steel |
| 3.9 | +8.1 | +0.016 | 0.000 | +0.016 | −0.035 | +0.216 |

The same microoxidation-corrosion test carried out on Fluid I without additives gave the results reported in the Comparative Example 1.

EXAMPLE 17

The starting material was a perfluoropolyether derivative of the formula $$CF_3O-(CF_2O)_6-CF_2COOCH_3$$

having a molecular weight of 590 and a boiling point of 120° C./15 Tor. 5 g of this ester were added to 1.5 g of aniline and the mixture was heated to 160° C. for 4 hours in an inert atmosphere. Subsequently, by distilling at reduced pressure, after removal of the formed $CH_3OH$ and the excess aniline, 4.8 g of a light yellow liquid were collected at 105° C./0.2 Tor; at room temperature the reaction product had a waxy consistency and was, however, very soluble in the perfluoroether fluids (N% calculated for the anilide $C_{15}H_6O_8NF_{17}$=2.16; N% found=2.15).

The compound obtained in this way when subjected to the test in the presence of $Al_2O_3$, mixed with the above defined Fluid I, gave the results shown in Table 7.

TABLE 7

| | | | |
|---|---|---|---|
| INHIBITION PERIOD AT 365° C. IN AIR IN THE PRESENCE OF 5% BY WEIGHT OF $Al_2O_3$ | | | |
| Anilide (% by weight) | Fluid I (% by weight) | Inhibition Period (minutes) | Rate of loss in weight during the I.P. (% per minute) |
| 2 | 98 | 345 | $0.8 \times 10^{-2}$ |
| 5 | 95 | <600 | $0.6 \times 10^{-2}$ |

EXAMPLE 18

The starting material was a polyperfluoroether derivative of the formula $$CF_3O-(C_3F_6O)_3-CF_2COF$$

having a molecular weight of 680.1, and a boiling point of 98° C./15 Tor.

10 g aniline were added to 20 g of this acid fluoride and the resulting mixture was gradually heated with stirring in a dry atmosphere for about 3 hours until reaching a temperature of 150° C. The final mass was filtered and the filtrate was distilled at reduced pressure. There were collected at 125° C./0.1 Tor, 19 g of a liquid which at room temperature had a waxy consistency. N%=1.84 (N% calculated for the anilide=1.86).

The thus obtained anilide, when subjected to the test with $Al_2O_3$ mixed with the above defined Fluid I, yielded the results indicated in Table 8.

TABLE 8

| | | | |
|---|---|---|---|
| INHIBITION PERIOD AT 365° C. IN AIR IN THE PRESENCE OF 5% BY WEIGHT OF $Al_2O_3$ | | | |
| Anilide (% by weight) | Fluid I (% by weight) | Inhibition Period (minutes) | Rate of loss in weight during the I.P. (% per minute) |
| 2 | 98 | 320 | $0.7 \times 10^{-2}$ |
| 5 | 95 | >600 | $0.4 \times 10^{-2}$ |

The same anilide mixed with Fluid I was subjected to the microoxidation-corrosion test described hereinbefore, and the results are given in Table 9.

TABLE 9

| Anilide (% by weight) | Loss (% in weight) | Variation % viscosity | Weight variation of the metals (mg/cm²) | | | | |
|---|---|---|---|---|---|---|---|
| | | | Ti alloy | Al alloy | Tool steel | Silver | Stainless steel |
| 5 | 0.11 | −0.0 | −0.02 | +0.03 | +0.11 | 0.00 | +0.04 |
| 2 | 0.16 | −0.7 | 0.00 | +0.03 | +0.13 | 0.00 | +0.04 |
| 1 | 0.23 | −1.1 | −0.01 | +0.02 | +0.13 | 0.00 | +0.06 |

MICROOXIDATION-CORROSION TEST AT 316° C. FOR 24 HOURS IN A FLOW OF ONE 1/H OF DRY AIR IN THE PRESENCE OF A STANDARD SERIES OF METALS AND THEIR ALLOYS

The same microxidation-corrosion test carried out on Fluid I without additives confirmed the results shown in Comparative Example 1.

EXAMPLE 19

The starting material was a polyfluoroether functional derivative of the formula $$CH_3OOC-CF_2-O-(CF_2CF_2O)_3-CF_2-COOCH_3$$

having a molecular weight of 582, and a boiling point of 230° C.

20 g of this diester were mixed with 8 g of aniline and the well-stirred mixture was heated to 150° C. for 4 hours. By subsequent rectification at reduced pressure, 22.5 g of a liquid gelling at room temperature, and containing N%=3.96 (calculated for the dianilide N%=3.98) were collected at 122° C./0.1 Tor. IR and NMR analysis showed that it was a pure dianilide. The dianilide thus obtained, when subjected to the test with $Al_2O_3$ mixed with the above defined Fluid III, yielded the results indicated in Table 10, which, for illustrative purposes, also gives the results obtained under the same conditions, using Fluid III without additives.

TABLE 10

| | | | |
|---|---|---|---|
| INHIBITION PERIOD AT 365° C. IN AIR IN THE PRESENCE OF 5% BY WEIGHT OF $Al_2O_3$ | | | |
| Dianilide (% by weight) | Fluid III (% by weight) | Inhibition Period (minutes) | Rate of loss in weight during the I.P. (% per minute) |
| 2 | 98 | 345 | $0.6 \times 10^{-2}$ |
| 5 | 95 | >600 | $0.4 \times 10^{-2}$ |
| 0 | 100 | 0 | 5 |

The same dianilide mixed with Fluid III was subjected to the microoxidation-corrosion test, the results of which are indicated in Table 11, which, for illustrative purposes, also gives the results of the same test carried out on Fluid III without additives.

TABLE 11

MICROOXIDATION-CORROSION TEST AT 316° C. FOR 24 HOURS IN A FLOW OF 1 1/H OF DRY AIR IN THE PRESENCE OF STANDARD SERIES OF METALS AND METAL ALLOYS

| Dianilide % by weight | Loss % in weight | Variation % viscosity | Weight variation of the metals (mg/cm²) | | | | |
|---|---|---|---|---|---|---|---|
| | | | Ti alloy | Al alloy | Tool steel | Silver | Stainless steel |
| 5 | 0.08 | 0.0 | +0.02 | +0.03 | +0.12 | 0.00 | +0.03 |
| 2 | 0.13 | −0.5 | +0.01 | +0.02 | +0.12 | 0.00 | +0.04 |
| 1 | 0.21 | −0.9 | −0.01 | +0.02 | +0.13 | 0.00 | +0.06 |

TABLE 11-continued

MICROOXIDATION-CORROSION TEST AT 316° C. FOR 24 HOURS IN A FLOW OF 1 l/H OF DRY AIR IN THE PRESENCE OF STANDARD SERIES OF METALS AND METAL ALLOYS

| Dianilide % by weight | Loss % in weight | Variation % viscosity | Weight variation of the metals (mg/cm$^2$) | | | | |
|---|---|---|---|---|---|---|---|
| | | | Ti alloy | Al alloy | Tool steel | Silver | Stainless steel |
| 0 | 46.5 | −97.8 | −0.21 | +0.16 | −1.19 | 0.00 | +0.78 |

EXAMPLE 20

The starting material was a pefluoropolyether functional derivative having the average composition $$X-O-(C_2F_4O)_{40}(CF_2O)_{70}-Y,$$

wherein, according to NMR spectroscopic examination, X and Y were mainly —CF$_2$—COF groups and, to a lesser extent, that is, less than 10%, they were perfluoroalkyl groups. The mixture contained individual compounds having from about 30 to about 200 perfluoroalkylene units.

1000 g of this mixture of acid difluorides and 130 g of phenothiazine were heated while stirring in a dry atmosphere at 180° C. for 5 hours. The reaction mixture was cooled to room temperature, filtered on a porous diaphragm, and the filtrate was heated to 330° C./0.2 Tor to distill away the excess phenothiazine.

The residue was filtered, to obtain 975 g of a colorless liquid having a nitrogen content of 0.28%. IR and NMR examination showed that the terminal groups were almost exclusively of the amide type, and few perfluoroalkyl terminal groups initially present being unchanged. The thus prepared amide compound, subjected to the test in the presence of Al$_2$O$_3$ alone or mixed with the above defined Fluid II, gave the results indicated in Table 12.

TABLE 12

INHIBITION PERIOD AT 365° C. IN AIR IN THE PRESENCE OF 5% BY WEIGHT OF Al$_2$O$_3$

| Diamide (% by weight) | Fluid II (% by weight) | Inhibition Period (minutes) | Rate of loss in weight during the I.P. (% by weight) |
|---|---|---|---|
| 2 | 98 | 105 | 1.7 × 10$^{-2}$ |
| 5 | 95 | 235 | 1.7 × 10$^{-2}$ |
| 10 | 90 | 480 | 0.7 × 10$^{-2}$ |
| 100 | 0 | >600 | 0.3 × 10$^{-2}$ |
| 0 | 100 | 0 | >5 |

Table 12, for comparative purposes, also reports the results obtained under the same conditions, using Fluid II without additives.

Variations can, of course, be made without departing from the spirit of the invention.

Having thus described our invention, what we desire to secure and claim by Letters Patent is:

1. A composition comprising (A) at least one perfluoropolyether fluid of the formula:

$$X-O-(C_3F_6O)_p-(CF_2O)_q-(C_2F_4O)_r-Y$$

wherein the perfluoroalkyleneoxy groups are randomly distributed along the chain; p, q and r are each zero or a number from 1 to 100 inclusive, the sum of p, q and r being 6 to 200; X and Y are the same or different from each other and are perfluoroalkyl groups having 1 to 3 carbon atoms; and (B) from 0.1 to 50 parts by weight per 100 parts of perfluoropolyether fluid of a perfluoropolyether compound having at least one arylamide terminal group and being of the formula:

$$A-O-(C_3F_6O)_P-(CF_2O)_Q-(C_2F_4O)_S-CF(Z)-CO-N(R)Ar$$

wherein if two or more of the perfluoroalkyleneoxy groups, (C$_3$F$_6$O), (CF$_2$O) and C$_2$Fhd 4O are simultaneously present in the chain, they are randomly distributed therealong; and wherein A is a perfluoroalkyl group having 1 to 3 carbon atoms or a —CF(Z)—CO—N(R)Ar group; P, Q and S are each zero but not simultaneously or a number ranging from 1 to 100 inclusive, the sum of P, Q and S being 3 to 200; Z is a fluorine atom or a CF$_3$ group; Ar is an unsubstituted aryl group, or an aryl group which is mono-, di- or tri-substituted with a lower alkyl group, an alkylaryl group, phenyl or halogen, and R is a hydrogen atom, a lower alkyl group, an unsubstituted phenyl or phenyl group which may be bound to Ar either directly or through a sulfur atom.

2. A composition as claimed in claim 1, wherein the amount of perfluoropolyether compound is from 1 to 20 parts per 100 parts by weight of perfluoropolyether fluid.

* * * * *

UNITED STATES PATENT OFFICE
CERTIFICATE OF CORRECTION

Patent No. 4,174,461      Dated Nov. 13, 1979

Inventor(s) Dario Sianesi et al

It is certified that error appears in the above-identified patent and that said Letters Patent are hereby corrected as shown below:

Column 9, Table 2, column 2, line 3: "beta-haphthylamine" should read -- beta-naphthylamine --.

Column 13, Table 7, column 3, last line: "<600" should read: -->600 --.

Column 15, Table 11, column 6, last line: "-1.19" should read -- -1.91 --.

Column 16, line 37: "$C_2Fhd4°$" should read -- $(C_2F_4O)$ --.

Signed and Sealed this

Seventh Day of October 1980

[SEAL]

Attest:

SIDNEY A. DIAMOND
Attesting Officer     Commissioner of Patents and Trademarks